US007870857B2

(12) United States Patent
Dhuper et al.

(10) Patent No.: US 7,870,857 B2
(45) Date of Patent: Jan. 18, 2011

(54) PATIENT INTERFACE ASSEMBLIES FOR USE IN VENTILATOR SYSTEMS TO DELIVER MEDICATION TO A PATIENT

(75) Inventors: Sunil Kumar Dhuper, Old Westbury, NY (US); Herbert Fred D'Alo, Madison, CT (US)

(73) Assignee: Aeon Research and Technology, Inc., Hewlett, NY (US)

( * ) Notice: Subject to any disclaimer, the term of this patent is extended or adjusted under 35 U.S.C. 154(b) by 732 days.

(21) Appl. No.: 11/418,392

(22) Filed: May 3, 2006

(65) Prior Publication Data

US 2006/0283447 A1     Dec. 21, 2006

Related U.S. Application Data

(60) Provisional application No. 60/684,142, filed on May 23, 2005.

(51) Int. Cl.
  *A61M 16/00*   (2006.01)
  *A61M 15/00*   (2006.01)
  *A62B 7/00*    (2006.01)
  *F23D 11/00*   (2006.01)

(52) U.S. Cl. .......................... 128/203.25; 128/203.12; 128/204.18; 128/203.26

(58) Field of Classification Search ............ 128/200.11, 128/200.24, 203.12, 203.13, 203.15–203.17, 128/203.25–203.27, 204.17, 204.18, 204.21, 128/205.11
See application file for complete search history.

(56) References Cited

U.S. PATENT DOCUMENTS

| 3,057,347 | A | * | 10/1962 | Mcgee | 128/202.28 |
|---|---|---|---|---|---|
| 4,463,755 | A | * | 8/1984 | Suzuki | 128/204.18 |
| 5,263,485 | A | * | 11/1993 | Hickey | 600/486 |
| 5,287,849 | A | | 2/1994 | Piper et al. | |
| 5,349,946 | A | * | 9/1994 | McComb | 128/203.17 |
| 5,388,571 | A | * | 2/1995 | Roberts et al. | 128/203.12 |
| 5,482,031 | A | * | 1/1996 | Lambert | 128/203.12 |
| 5,628,305 | A | * | 5/1997 | Melker | 128/202.29 |
| 5,640,951 | A | * | 6/1997 | Huddart et al. | 128/204.17 |
| 5,791,340 | A | | 8/1998 | Schleufe et al. | |
| 5,813,423 | A | * | 9/1998 | Kirchgeorg | 128/202.28 |
| 5,848,587 | A | | 12/1998 | King | |
| 5,865,172 | A | | 2/1999 | Butler et al. | |
| 6,039,042 | A | | 3/2000 | Sladek | |
| 6,041,777 | A | * | 3/2000 | Faithfull et al. | 128/200.24 |
| 6,078,730 | A | * | 6/2000 | Huddart et al. | 392/480 |
| 6,192,884 | B1 | | 2/2001 | Vann et al. | |
| 6,427,685 | B1 | * | 8/2002 | Ray, II | 128/200.24 |
| 6,494,202 | B2 | | 12/2002 | Farmer | |

(Continued)

*Primary Examiner*—Steven O Douglas
*Assistant Examiner*—Rachel T Young
(74) *Attorney, Agent, or Firm*—Leason Ellis LLP

(57) ABSTRACT

According to one aspect of the present invention, a ventilator system includes (a) a ventilator device having an inhalation port and exhalation port; (b) a patient conduit for delivering to and removing gas from the patient; (c) an exhalation conduit fluidly connected to the exhalation port and the patient conduit; (d) an inhalation conduit fluidly connected to the inhalation port and the patient conduit; and (e) a device for generating aerosolized medication, the device being fluidly connected to the inhalation conduit so that the aerosolized medication is delivered to the patient as the patient inhales. According to the present invention, at least the inhalation conduit has a variable length to position the device for generating aerosolized medication a predetermined distance from the patient conduit.

27 Claims, 8 Drawing Sheets

U.S. PATENT DOCUMENTS

| | | |
|---|---|---|
| 6,550,476 B1 | 4/2003 | Ryder |
| 6,622,725 B1 * | 9/2003 | Fisher et al. ............ 128/204.21 |
| 6,776,160 B2 | 8/2004 | Wang |
| 6,799,423 B2 | 10/2004 | Piekarski |
| 6,976,488 B2 * | 12/2005 | Halperin ................ 128/201.13 |
| 2002/0017302 A1 * | 2/2002 | Fukunaga et al. ....... 128/207.14 |
| 2003/0010336 A1 * | 1/2003 | Vito ..................... 128/200.22 |
| 2003/0209246 A1 * | 11/2003 | Schroeder et al. ...... 128/204.17 |
| 2004/0011364 A1 | 1/2004 | Dhuper et al. |
| 2004/0024372 A1 * | 2/2004 | Grogan ....................... 604/295 |
| 2004/0123974 A1 | 7/2004 | Marler et al. |
| 2005/0039747 A1 * | 2/2005 | Fukunaga et al. ....... 128/204.18 |
| 2005/0092325 A1 * | 5/2005 | Dionne .................. 128/205.25 |
| 2005/0092329 A1 * | 5/2005 | Sta-Maria .............. 128/207.18 |

* cited by examiner

PATIENT INTERFACE ASSEMBLIES FOR USE IN VENTILATOR SYSTEMS TO DELIVER MEDICATION TO A PATIENT

CROSS-REFERENCE TO RELATED APPLICATION

The present application claims the benefit of U.S. patent application Ser. No. 60/684,142, filed May 23, 2005, which is hereby expressly incorporated by reference in its entirety.

TECHNICAL FIELD

The present invention relates to inhalation equipment and more particularly, relates to a ventilator system that integrally incorporates a means for generating aerosolized medication into the inhalation flow path and also provides means for changing the location of the means for generating aerosolized medication relative to the patient in view of certain parameters, such as patient body weight, etc.

BACKGROUND

A ventilator is an automatic mechanical device designed to provide all or part of the work the body must produce to move gas into and out of the lungs. The act of moving air into and out of the lungs is called breathing, or, more formally, is called ventilation. During breathing, a volume of air is inhaled through the airways (mouth and/or nose, pharynx, larynx, trachea, and bronchial tree) into millions of tiny gas exchange sacs (which are called the alveoli) deep within the lungs. There it mixes with the carbon dioxide-rich gas coming from the blood. It is then exhaled back through the same airways to the atmosphere. Normally this cyclic pattern repeats at a breathing rate, or frequency, of a number of breaths per minute (breaths/min) which differs depending upon our environment. For example, the breathing rate is lower when we are at rest (however a higher resting rate for infants and children) and increases when we exercise or become excited.

Gas exchange is the function of the lungs that is required to supply oxygen to the blood for distribution to the cells of the body, and to remove carbon dioxide from the blood that has been collected from the cells of the body. Gas exchange in the lungs occurs only in the smallest airways and the alveoli. It does not take place in the airways (conducting airways) that carry the gas from the atmosphere to these terminal regions. One of the major factors determining whether breathing is producing enough gas exchange to keep a person alive is the 'ventilation' the breathing is producing. Ventilation is expressed as the volume of gas entering, or leaving, the lungs in a given amount of time. It can be calculated by multiplying the volume of gas, either inhaled or exhaled during a breath (called the tidal volume), times the breathing rate.

Thus, the mechanical ventilator is constructed to help a person breathe, or to take over his or her breathing altogether. As a result, the ventilator has to be able to produce a tidal volume and a breathing rate which, when multiplied together, produce enough ventilation, but not too much ventilation, to supply the gas exchange requirements of the body.

Conventional ventilators typically include a number of working components that cooperate with one another to ensure the desired action is realized. More specifically, a conventional ventilator includes a stable attachment (also called an interface or accessory) of the device to the patient; a source of energy to drive the device; a control system to make it perform appropriately; and a means of monitoring the performance of the device and the condition of the patient. The ventilator delivers gas to the patient through a set of flexible conduits or tubes called a patient circuit. Typically, the ventilator includes two tubes one associated with exhalation and the other associated with inhalation; however, the ventilator can include one tube. The circuit connects the ventilator to either an endotracheal or tracheostomy tube that extends into the patient's throat (in the case of an invasive ventilation), or a mask covering the mouth and nose or just the nose (in the case of a noninvasive ventilation).

The ventilator is powered by a power source, such as electricity or compressed gas. Electricity can used to run a compressor that provides compressed air for breathing; however, it is more common for the power to expand the lungs to be supplied by compressed gas from tanks, or from wall outlets in a hospital or the like. Because compressed gas has all moisture removed, the gas delivered to the patient must be warmed and humidified in order to avoid drying out the lung tissue. To accomplish this, a humidifier is placed in the patient circuit and the use of a humidifier is especially needed when an endotracheal or tracheostomy tube is used since these cover or bypass, respectively, the warm, moist tissues inside of the nose and mouth and prevent the natural heating and humidification of the inspired gas.

The ventilator includes a control system that assures that the breathing pattern produced by the ventilator is the one intended. This requires the setting of control parameters such as the size of the breath, how fast and how often it is brought in and let out, and how much effort, if any, the patient must exert to signal the ventilator to start a breath.

The ventilator also preferably includes monitor devices which monitor how the ventilation operation is proceeding. Typically, most ventilators have at least a pressure monitor (measuring airway pressure for positive pressure ventilators, or chamber pressure for negative pressure ventilators) to gauge the size of the breath and whether or not the patient is properly connected to the ventilator. One other type of monitoring system is the use of a temperature probe to continuously monitor the temperature within both the inhalation and exhalation tubes and in particular, the system compares the temperature within the tube at a distal end and a proximal end which is close to or at the location of the humidifier. If the temperature at the distal end is not approximately the same as the temperature at the proximal end or within some threshold range, the heating coils or wires associated with the humidifier can be activated to elevate the temperature inside the tube.

One of the problems associated with conventional ventilator design is the means by which medication is delivered into the ventilator system. In an arrangement where the ventilator has an inhalation tube and exhalation tube, the exhalation tube is connected at its proximal end to an exhalation port of the ventilator and is connected at its distal end to one leg of a Y-shaped connector or adaptor. Similarly, the inhalation tube is connected at its proximal end to an inhalation port of the ventilator and is connected at its distal end to the other leg of the Y-shaped connector or adaptor. Along the length of the inhalation tube, the humidifier is provided for heating and adding moisture to the air delivered to the patient. One means for heating the inside of the tubes is the use of heating wires or coils that are provided along a length of the tube.

When it is necessary to deliver medication to the patient using either a metered dose inhaler (MDI) or a nebulizer, the physician must disconnect the distal end of the inhalation tube from the leg of the Y-connector and then insert an MDI unit or a nebulizer using a nebulizer T connector before closing off the circuit with the inserted MDI or nebulizer. It will be appreciated that at this location, the MDI or nebulizer is very close to the endotracheal or tracheostomy tube and this is actually a disadvantage for several reasons described below.

While the Y-connector can include a port that serves as an attachment to the MDI, the Y-connector is not constructed for coupling to the nebulizer T connector. Thus, the nebulizer T must be placed within the inhalation tube circuit by disconnecting the tube from the Y-connector and then inserting the nebulizer T connector before reconnecting the inhalation tube and the Y-connector to legs of the nebulizer T connector. When a nebulizer is used in the conventional arrangement, the nebulizer is incorporated into the circuit of the ventilator by providing a tube that attaches to a port of the ventilator at one end and attaches to the nebulizer at the other end. This tube carries gas produced by the ventilator to the nebulizer where it is used to aerosolize the medication which is then delivered to the patient. The nebulizer thus operates using an inside source of gas, namely gas that is produced from the ventilator. Because an inside source of gas is used and the nebulizer is subject to the flow limitations of the ventilator itself, the dose of medication delivered to the patient over a fixed time is low. In other words, it takes a significant time for the medication to be completely aerosolized and delivered to the inhalation tube.

One of the disadvantages of the conventional design is that the inclusion of a fixed volume holding chamber does not accommodate the specific needs of the particular patient that is being treated with the ventilator. For example, a holding chamber that is suitable for an infant is not suitable for an adult and vice versa. Thus, the fixed holding chamber construction can not accommodate all types of patients.

The only other spot in the conventional configuration for the MDI or nebulizer to be inserted is at the interface between the inhalation tube and the humidifier. However, at this location, the medication is delivered at a location that is far away from the endotracheal or tracheostomy tube and this leads to a number of problems in that as the medication flows along the length of the inhalation tube, the medication is deposited along the inside of the tube and is not delivered to the patient. In other words, aerosolized particles attach to the inside of the inhalation tube.

What is needed in the art and has heretofore not been available is a system that overcomes the above deficiencies and incorporates functionality to make the device a compact, user friendly, economical, and multipurpose ventilator system for both acute and chronic use with either an MDI or a nebulizer or with both devices simultaneously as warranted by the patient's clinical circumstances.

SUMMARY

According to one aspect of the present invention, a ventilator system includes (a) a ventilator device having an inhalation port and exhalation port; (b) a patient conduit for delivering to and removing gas from the patient; (c) an exhalation conduit fluidly connected to the exhalation port and the patient conduit; (d) an inhalation conduit fluidly connected to the inhalation port and the patient conduit; and (e) a device for generating aerosolized medication, the device being fluidly connected to the inhalation conduit so that the aerosolized medication is delivered to the patient as the patient inhales. According to the present invention, at least the inhalation conduit has a variable length to position the device for generating aerosolized medication a predetermined distance from the patient conduit.

The inhalation conduit defines in part a holding chamber that has an adjustable interior volume due to the variable length of the conduit and therefore, the volume of the inhalation conduit can be advantageously varied depending upon a number of different parameters, such as the type of patient and more specifically, the weight of the patient. The volume can be varied by simply either expanding or contracting the inhalation conduit given its structure that permits such event to occur. There is a direct correlation between the weight of the patient, and lung capacity, and the volume of the holding chamber in that the greater the weight of the patient, the greater the required volume of the holding chamber. In accordance with one aspect of the invention, the volume of the holding chamber can be chosen between a number of different selected volumes so as to cater and customize the present system for a specific patient.

In another aspect and embodiment, a ventilator system includes: (a) a ventilator device having an inhalation port and exhalation port; (b) a patient conduit for delivering to and removing gas from the patient; (c) a heat moisture exchanger in fluid communication with the ventilator device; (d) a first exhalation conduit fluidly connected to the exhalation port and the heat moisture exchanger; (e) a first inhalation conduit fluidly connected to the inhalation port and the heat moisture exchanger; (f) a second exhalation conduit fluidly connected to the patient conduit and the heat moisture exchanger; (g) a second inhalation conduit fluidly connected to the patient conduit and the heat moisture exchanger; and (h) a device for generating aerosolized medication, the device being fluidly connected between the second inhalation conduit and the heat moisture exchanger so that the aerosolized medication is delivered to the patient as the patient inhales. According to this embodiment, at least the second inhalation conduit has a variable length to position the device for generating aerosolized medication a predetermined distance from the patient conduit.

Further aspects and features of the exemplary ventilator system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF THE PREFERRED EMBODIMENTS

Figure 1:
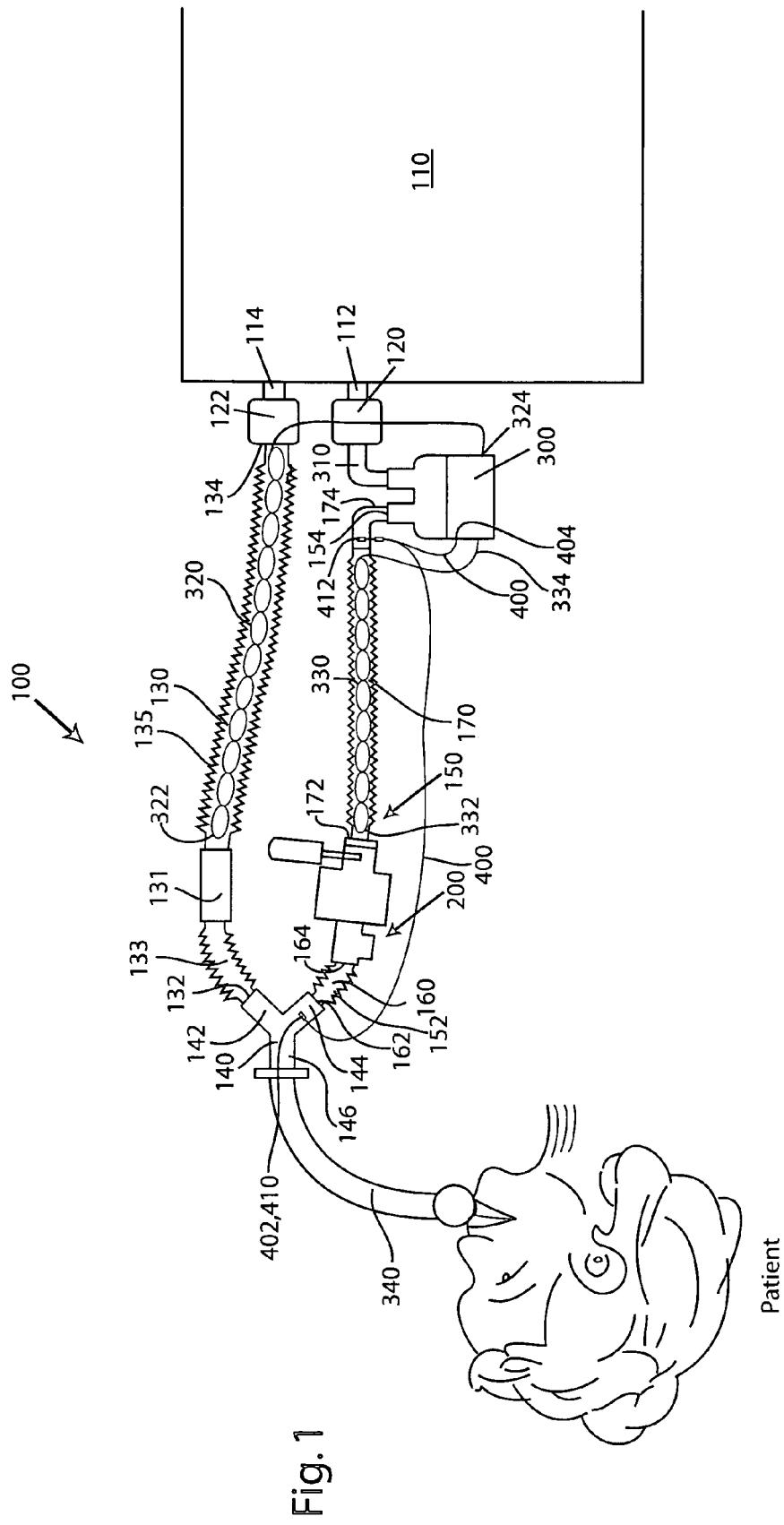
FIG. 1 is a cross-sectional side elevation view of a ventilator system according to a first embodiment.
Figure 2:
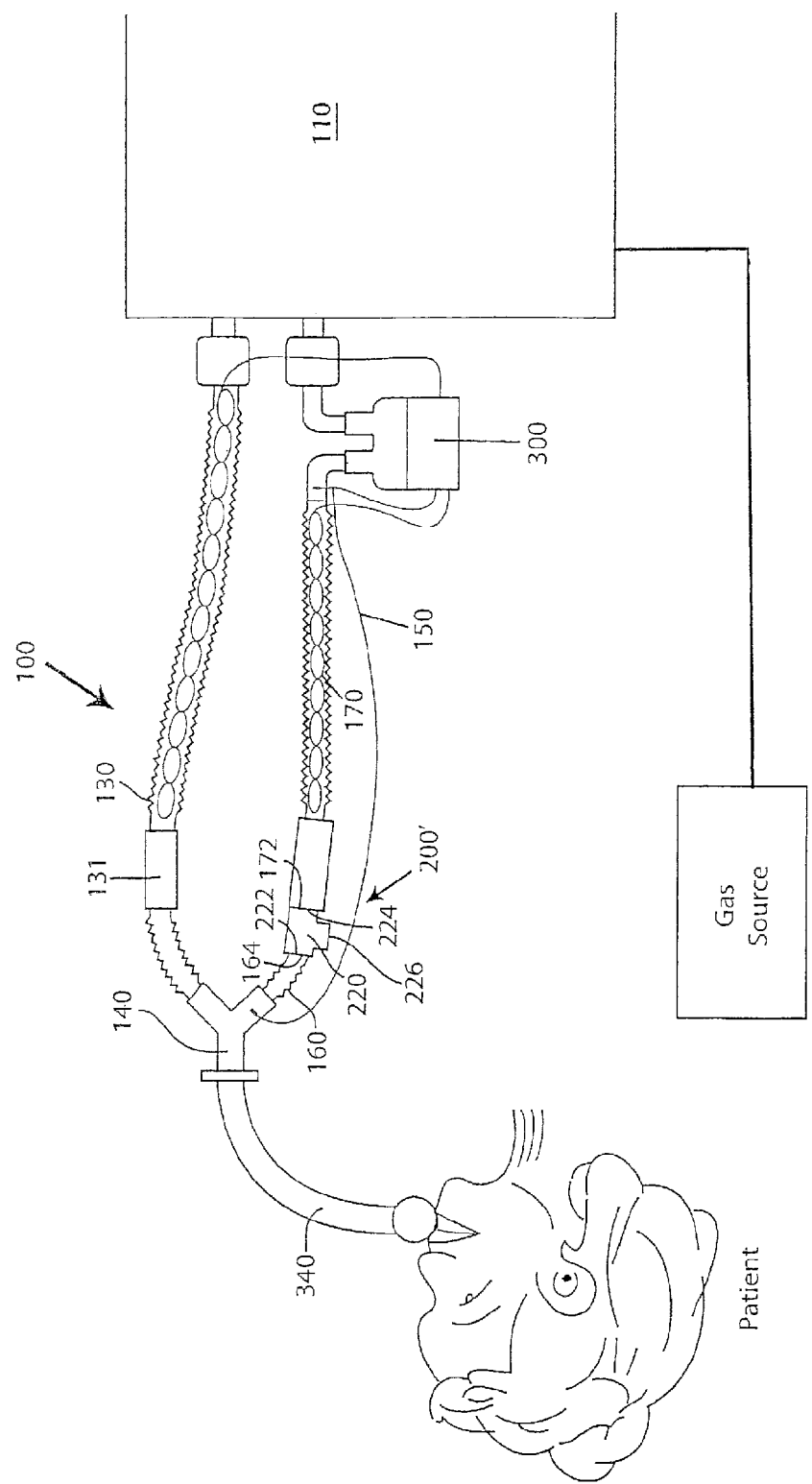
FIG. 2 is a cross-sectional side elevation view of a ventilator system according to a second embodiment.
Figure 3:
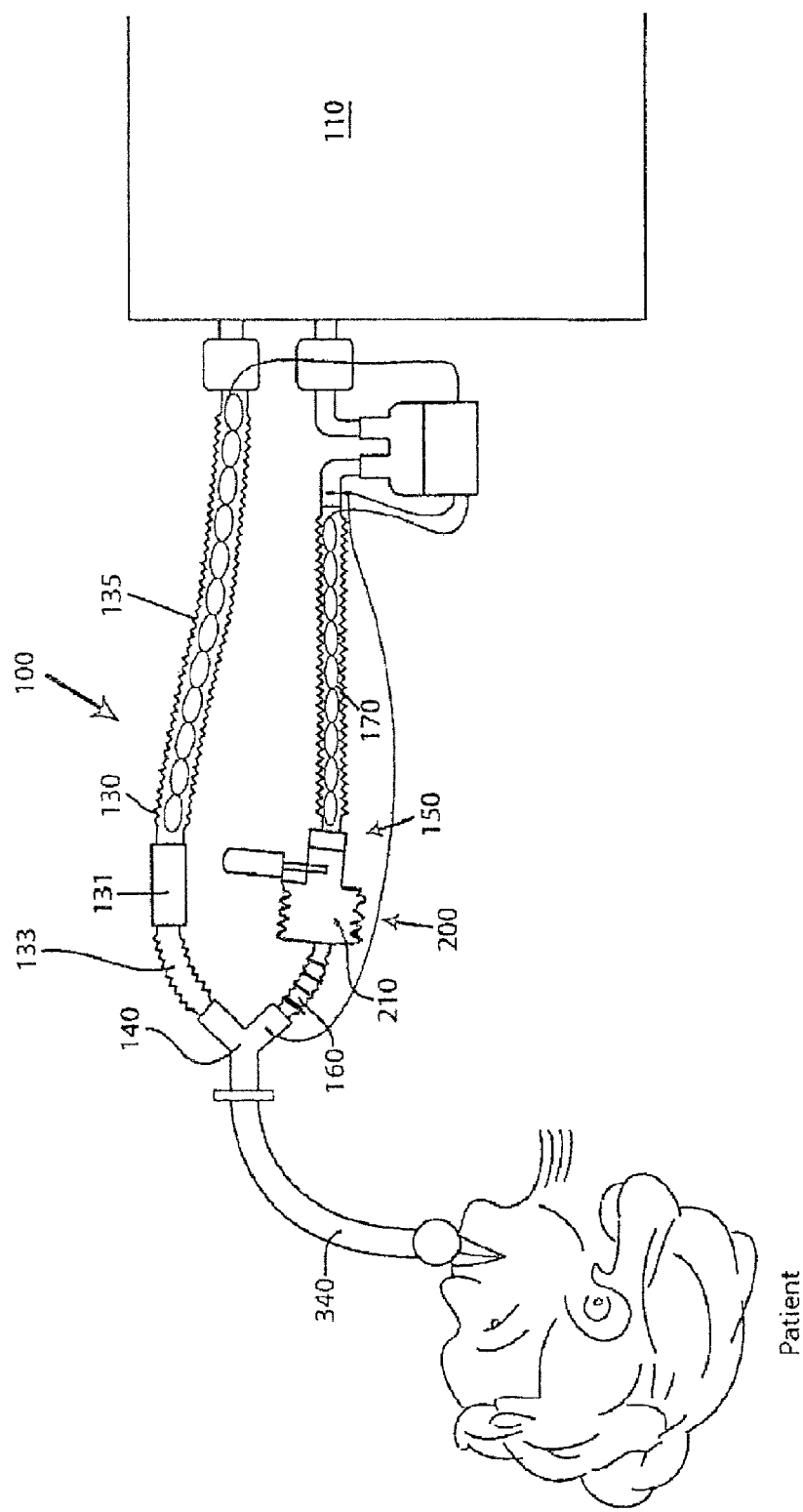
FIG. 3 is a cross-sectional side elevation view of a ventilator system according to a third embodiment.

Now turning to FIGS. 1-3 in which a ventilator system 100 according to one exemplary embodiment is illustrated. The system 100 includes a ventilator device 110 which can be any number of commercially available ventilators. The ventilator device 110 has a first port 112 which serves as an inhalation port and a second port 114 which serves as an exhalation port. The ventilator device 110 includes a first valve 120 that is associated with the inhalation port 112 and a second valve 122 that is associated with the exhalation port 114. As will be understood below, when a patient inhales, the first valve 120 opens, while the second valve 122 closes so as to permit the generated gas to flow to the patient to assist in the patient's breathing. Conversely, when the patient exhales, the first valve 120 assumes a closed position and the second valve 122 opens so as to permit exhaled gas to be delivered from the patient back to the ventilator. The first and second valves 120, 122 can therefore be in the form of one-way valves or the like.

The ventilator system 100 further includes a first conduit 130 that has a first end 132 and an opposing second end 134. The first end 132 can be thought of as the distal end, while the second end 134 can be thought of as a proximal end. In the embodiment of FIG. 1, the first tube 130 acts as the exhalation tube of the ventilator system 100, with the second end 134 being operatively and sealingly coupled to the exhalation port 114. The first end 132 is operatively and sealingly coupled to a first leg 142 of a Y-connector 140. The ventilator system 100 also includes a second conduit 150 that has a first end 152 and an opposing second end 154. The first end 152 can be though of as the distal end, while the second end 154 can be thought as the proximal end of the second conduit 150. The second conduit 150 acts as the inhalation tube of the ventilator system 100.

According to one aspect of the present invention, the second conduit 150 is actually formed of two sections, namely, a first conduit section 160 and a second conduit section 170. The second conduit 150 is thus divided into the two sections 160, 170 in order to permit one or more interface accessories to be placed in-line along the inhalation conduit 150. The first conduit section 160 is a more distal section and includes a first end 162 that is attached to a second leg 144 of the Y-connector 140 and a second end 164 that is attached to at least one device for delivering medication to the patient (means for delivering medication) 200. The second section 170 includes a first end 172 that is attached to the device 200 and a second end 174 is attached to a port 302 of a humidifier unit 300. The humidifier unit 300 is operatively connected to the ventilator device 110 by means of an interface or conduit 310 so that compressed gas is delivered from the ventilator device 110 to the humidifier unit 300.

As previously mentioned, the humidifier unit 300 acts to heat and add moisture to the air delivered to the patient through the inhalation tube 150. One means for heating the inside of the tubes is the use of heating wires or coils that are provided along a length of the tubes. More specifically, a first heating wire 320 is provided within the interior of the first conduit 130 for controlled heating thereof. The first heating wire 320 has a distal end 322 that is disposed within the interior of the first conduit 130 while a proximal end 324 is operatively connected to the humidifier unit 300 in such a way that the heating wire 320 can be controllably heated to a predetermined temperature. Preferably, the first heating wire 320 is incorporated into the inner walls of the first conduit 130 and can be arranged according to any number of different shapes or configurations. For example, the first heating wire 320 can be arranged in a helical manner within the interior of the first conduit 130 or it can be arranged in coiled manner or it can be arranged in any number of other arrangements so long as a significant length of the first conduit 130 can be heated to a predetermined temperature that is substantially constant along the length thereof.

A second heating wire 330 is provided within the interior of the second section 170 of the second conduit 150 for controlled heating thereof. The second heating wire 330 has a distal end 332 that is disposed within the interior of the second section 170 proximate the first end 172 of the second section 170, while a proximal end 334 of the second heating wire 330 is operatively connected to the humidifier unit 300 in such a way that the second heating wire 330 can be controllably heated to a predetermined temperature. Preferably, the second heating wire 330 is incorporated into the inner walls of the second section 170 of the second conduit 150 in the same manner as the first heating wire 320 is incorporated in the first conduit 130, e.g., helical manner, coiled manner, etc.

Figure 8:
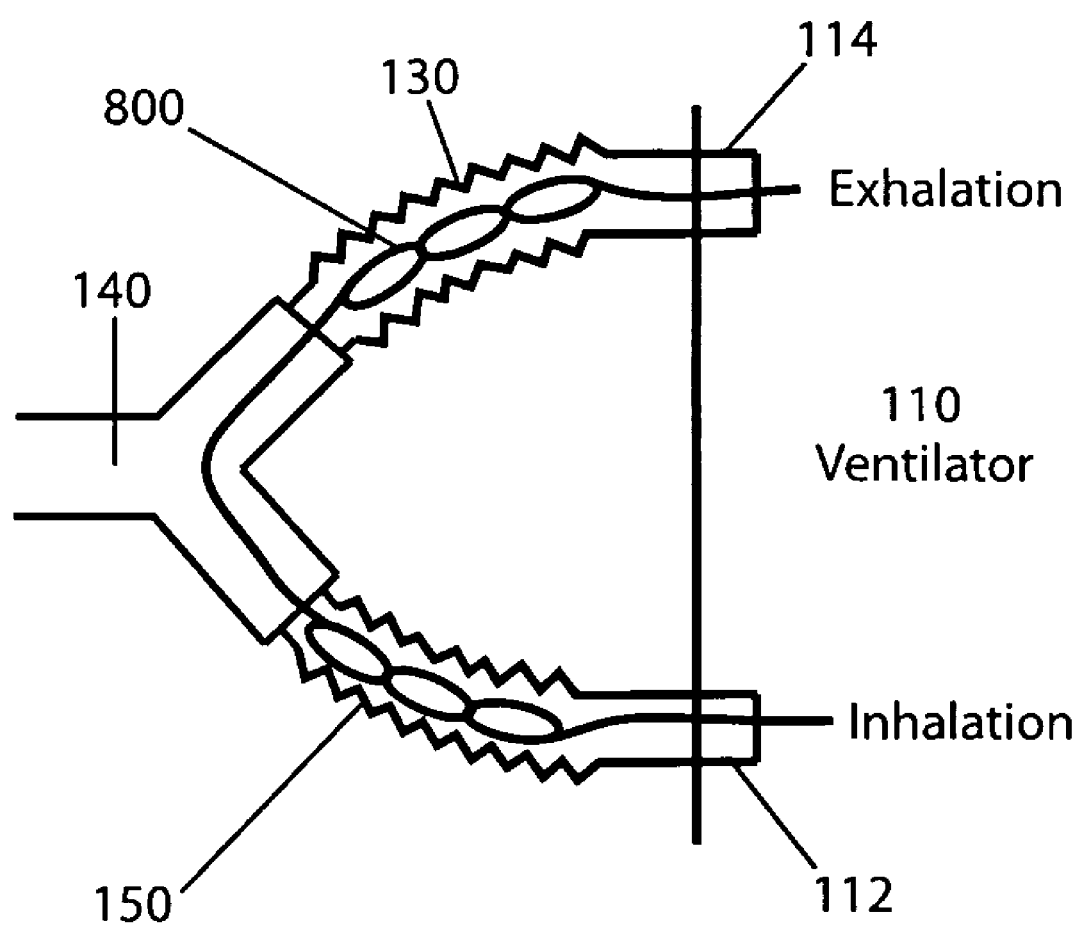
FIG. 8 is a close-up cross-sectional side elevation view of an alternative heating wire arrangement for the system of FIG. 1.

The first and second heating wires 320, 330 can be conventional ventilator heating wires that are available from a number of commercial sources. In addition, it will further be appreciated that the first and second heating wires 320, 330 can be combined into a single heating wire 800 as shown in FIG. 8 where the single coiled heating wire 800 runs along both the inhalation tube 150 and the exhalation tube 130. In this embodiment, the coiled heating wire is routed along one of the tubes 130, 150 and is then looped back and routed along the other of the tubes 130, 150.

The humidifier unit 300 also typically includes a temperature probe 400 that is used in combination with the first and second heating wires 320, 330 to monitor and control the temperature within the inhalation tube 150. The temperature probe 400 is an elongated structure that is routed along the second section 170 of the inhalation tube 150. For example, the illustrated temperature probe 400 can be a temperature probe wire that has a first end 402 and a second end 404. The first end 402 has a first temperature sensor 410 associated therewith, while the second end 404 has a second temperature sensor 412 associated therewith. The first temperature sensor 410 is preferably positioned close to the connection between the device 200 and the first end 172 of the second section 170, while the second temperature sensor 412 is preferably positioned close to the connection between the second end 174 and the humidifier unit 300. In one embodiment, small openings are formed through the second section 170 near or at its ends 172, 174 to receive, accommodate and hold the sensors 410, 412 such that the sensing surface of the sensors 410, 412 is placed within the interior of the second section 170 and is capable of accurately sensing the temperature therein. When the sensors 410, 412 are disposed in openings formed in the second section, the length of the temperature probe wire 400 between the two sensors 410, 412 is routed along the exterior of the second section 170.

The humidifier unit 300 and the master control unit of the ventilator device 110 are constructed so that the temperature within at least the inhalation tube 150 is maintained relatively constant at a predetermined temperature. By placing one sensor 410 at the distal end and the other sensor 412 near the humidifier unit 300 itself, the temperature at the two opposing ends of the inhalation tube 150 can be monitored. If the temperature of the air leaving the second section 170 is not approximately the same or is not within a threshold range compared to the temperature of the air entering the second section 170, then the humidifier unit 300 raises the temperature within the second section 170 by increasing the energy in the second heating wire 330.

The Y-connector 140 has a third leg 146 that is connected to a conduit 340 that leads directly to the patient. More specifically, the third leg 146 can be attached to an endotracheal or tracheostomy tube 340 that leads to the patient. As with Y-connectors, the first and second legs 142, 144 form the open Y-end of the connector 140 and space the inhalation tube 150 apart from the exhalation tube 130.

According to one aspect of the present invention, the means for generating aerosolized medication 200 is directly incorporated into the inhalation conduit of the circuit and therefore, unlike conventional ventilation design, the physician does not have to remove and reconfigure the inhalation tube 150 in order to incorporate the device 200 within the inhalation gas path. The accessory 200 can be any number of different devices that are intended to deliver medication to the patient as illustrated in FIGS. 1-3, where FIG. 2 includes one device type, FIG. 3 includes another device type; and FIG. 1 illustrates a combination of the devices of FIGS. 2 and 3. In one embodiment, shown in FIG. 1A, the device 200 is in the form of an MDI assembly which is essentially a pressurized canister that contains a medication and propellant. Actuation of the MDI 200 results in the discharge of one dose of medication as aerosolized particles, which can be spontaneously inhaled by the patient or delivered in conjunction with positive-pressure breaths. A spacer device/accessory device 210 should be used with the MDI device 200. The spacer device 210 enhances delivery by decreasing the velocity of the particles and reducing the number of large particles. As can be seen in FIG. 3, the spacer 210 is in fluid communication with the first section 160 of the second conduit 150 and therefore, the aerosolized particles that are generated by the MDI device 200 are discharged into the first section 160 where they flow into the endotracheal tube 340 to the patient. As with most MDI assemblies, the MDI 200 of FIG. 3 includes a nozzle with a canister stem that permit actuation of the MDI 200.

In another embodiment shown in FIG. 2, the means for generating aerosolized medication 200 is in the form of a nebulizer 200'. In general, aerosol delivery systems that use standard small volume nebulizers 200' are commonly used in acute conditions as they are relatively inexpensive; however, the medication dose used is about 10 times of that used with an MDI and hence there is potentially an increased cost without any added proven clinical benefit. Another difficulty with nebulizers as mentioned above is that the majority of the nebulized medication is wasted during exhalation since when the patient exhales, the medication can travel from the holding chamber into the exhalation tube 130. Moreover, the time taken to deliver the medication is several times that of an MDI and the labor cost of respiratory therapist may outweigh the benefits of nebulizers compared with MDIs.

Many of these devices 200' are commercially available in which the nebulizer is directly attached to a T connector 220 without any mixing chamber. In FIG. 2, the T connector 220 includes a first leg 222 that is attached to the second end 164 of the first section 160 of the second conduit 150 and a second leg 224 that is attached to the first end 172 of the second section 170 of the second conduit 150. A third leg 226 that is typically perpendicular to an axis through the first and second legs 222, 224 is used to connect to a source of gas 230. Unlike conventional arrangements between a nebulizer and a ventilator, the nebulizer 200' of the present invention uses a continuous source of gas 230 as opposed to using gas generated by the ventilator device 110 (inside source). The continuous source of gas 230 can be an outside or external source of gas that is hooked up to the third leg 226 such that a continuous stream of gas is delivered to the nebulizer 200'. Alternatively, it will be appreciated that the continuous source of gas 230 can be an internal source and can be in the form of an additional port or interface in the ventilator device 210 that provides a continuous flow of gas both during inhalation and exhalation. In the existing schemes, a nebulizer that is connected to the ventilator device 210 for its source of gas is only provided with a stream of gas during inhalation by the patient and therefore more time is needed to completely aerosolize the medication since the gas does not flow continuously.

According to one aspect, the present invention permits the physician to adjust either the location of the MDI 200 and/or nebulizer 200' as a means for adjusting the strength of the dose of medication that is administered to the patient.

In addition, since the MDI 200 and/or the nebulizer 200' are part of the inhalation tube 150, the inhalation tube 150 does not have to be detached and therefore, the associated risk of infection due to contamination of the inhalation tube 150 is eliminated. In the conventional arrangement, when the MDI 200 or the nebulizer 200' was attached to the inhalation tube 150, there was a risk of infection since this task required that the inhalation tube 150 be disconnected and thus, foreign contaminants could access the interior of the inhalation tube 150.

When the MDI 200 and the nebulizer 200' are used in combination as shown in FIG. 1 and are both provided within the inhalation circuit, the third leg 226 of the nebulizer 200' can be simply capped when the MDI 200 is in use. In this configuration, the second leg 224 is fluidly connected to the spacer 210 and therefore, the MDI 200 and the nebulizer 200' are arranged in series with respect to one another.

In another aspect of the present invention, one or more of the first and second conduits 130, 150 have an adjustable length in that the conduit is formed of a material and has a construction and configuration that permits the conduit to be adjusted between a fully expanded condition where the conduit is at its maximum length and a fully retracted or compressed condition where the conduit is at is minimum length. There are a number of different types of constructions that will permit the conduit to function in this way. For example, the wall of the conduit can be in the form of a bellows type structure which is easily compacted or compressed to reduce the length of the conduit, and equally can be easily expanded or stretched to increase the length of the conduit.

FIGS. 1-3 illustrate a bellows type structure for both the inhalation tube 150 and the exhalation tube 130. Even when the exhalation tube 130 has an expandable/compressible structure, the exhalation tube 130 can optionally include a rigid section 131 that in effect partitions the exhalation tube 130 into a first section 133 that extends between the first leg 142 of the Y-connector 140 and the rigid section 131 and a second section 135 that extends between the rigid section 131 and the exhalation port 114 of the ventilation device 110. The bellows type structure can be formed from any number of different materials, including but not limited to a plastic material, a fabric or a metal material. It will be understood that while the illustrated embodiment shows both the first and second sections 133, 135 as being expandable/compressible in nature, one or both of these sections can be a rigid structure that does not have a variable length.

Similarly, one or more of the first and second sections 160, 170 of the second conduit 150 (inhalation tube) can have a variable length such that the section is positionable between a fully extended condition and a fully compact condition. As with the first conduit 130, the second conduit 150 can have a bellows type structure or any other structure that permits the second conduit 150 to expand and contract so as to either increase or reduce the length of the second conduit 150. The structure of each of the first and second heating wires 320, 330 is such that the heating wires easily expand and contract as either the inhalation or exhalation tube expands and contracts, respectively. For example, the heating wires 320, 330 can be incorporated into the tube in a coiled manner such that that when the tube expands, the turns of the coil accommodate such movement and spread apart further from one another. Similarly, when the turns of the coil accommodate contracts of the tube by having the coils come together.

It will be understood that the first section 160 of the second conduit 150 acts as a reservoir for the medication as the patient both inhales and exhales since the first section 160 is disposed between the Y-connector 140, as well as the endotracheal tube 340, and the means for delivering medication to the patient which can be in the form of the MDI 200 and/or the nebulizer 200'. It will also be appreciated that the spacer 210 of the MDI 200 has a variable volume since similar to the tubes 130, 150, the spacer 210 is constructed so that it has a variable length as by incorporating a bellows type wall structure or the like into the spacer 210 design. Alternatively, the spacer 210 can be formed of two parts that are slidable with respect to one another so as to vary the interior volume (holding chamber) defined therein. More specifically, one part can be slideably received within the other part so as to define an interior volume that can be adjusted by merely moving one part relative to the other part.

Unlike conventional designs where the location of the MDI 200 and/or nebulizer 200' is fixed to one or two locations, the system 100 of the present invention permits the distance from the endotracheal tube 340 to the MDI 200 or the nebulizer 200' to be varied. In other words, the present invention provides an inhalation circuit that can either be expanded or contracted so as to position the MDI 200 and/or the nebulizer 200' at a desired distance from the endotracheal tube 340.

Since the temperature probe 400 has a fixed length, the expansion and contraction of the inhalation tube 150 has to take this into account and more particularly and according to one embodiment, the extension of the first section 160 is offset by contracting the second section 170 of the inhalation tube 150. The first section 160 can be constructed so that it can be extended any where from several inches up to a number of feet, such as 5 feet. In one embodiment, the length of the second section 170 is reduced by the same distance that the first section 160 is expanded in order to position the MDI 200 and/or nebulizer 200' at a location that is further away from the Y-connector 340. This serves to position the MDI 200 and/or nebulizer 200' further away from the endotracheal tube 340. It will be understood that in effect, the distance between the humidifier unit 300 to the endotracheal tube 340 can remain substantially the same with only the ratio of the distances between the endotracheal tube 340 and the MDI 200/nebulizer 200' and between the MDI 200/nebulizer 200' and humidifier unit 300 being varied.

According to the present invention, the inhalation tube 150 defines in part a holding chamber that has an adjustable interior volume and therefore, the volume of the inhalation tube 150, especially the first section 160 thereof, can be advantageously varied depending upon a number of different parameters, such as the type of patient and more specifically, the weight of the patient. The volume can be varied by simply either expanding or contracting the inhalation tube 150 given its structure that permits such event to occur. There is a direct correlation between the weight of the patient, and lung capacity, and the volume of the holding chamber (defined in part by first section 160) in that the greater the weight of the patient, the greater the required volume of the holding chamber. In accordance with one aspect of the invention, the volume of the holding chamber can be chosen between a number of different selected volumes so as to cater and customize the system 100 for the specific patient. The different settings can be marked on the first section 160 or they can be otherwise conveyed to the physician who then merely manipulates the first section 160 so that the volume of the holding chamber is within the desired range.

For example, the settings corresponding to the volume of the holding chamber, which in turn corresponds to the length of the first section 160, can be (1) infant; (2) young child; (3) pre-teen child; (4) teenager; (5) young adult; (6) adult; and (7) elderly. Similarly, the settings corresponding to the volume of the holding chamber can be directly correlated to a mass size, such as (1) less than 20 pounds; (2) less than 60 pounds; (3) less than 100 pounds; (4) less than 150 pounds; (5) less than 200 pounds, etc. After determining what the proper setting should be, the physician can then manipulate the length of the first section 170 to cause the volume within the holding chamber defined thereby to be set at the desired value. In each of the embodiments, the first section 160 can be manually manipulated resulting in the interior volume of the first holding chamber either being increased or decreased. For example and according to one embodiment, the first section 160 can have a number of markings, settings, or graduations so that it is easy for the user to simple adjust the first section 160 relative to a fixed component, such as the Y-connector 140 until the desired marking is visible. For example, if the patient is a heavy set adult, the physician can position the MDI 200 and/or nebulizer 200' further away from the Y-connector 140 and the endotracheal tube 340 by simply extending the first section 170 to a desired length. Preferably, the first section 170 can be extended any where from several inches all the way up to five feet or more depending upon the particular application.

The extendable/contractable nature of the exhalation tube 130 is designed more to accommodate the extension or contraction of the inhalation tube 150 since the exhalation tube 130 does not contain a device like the MDI 200 or nebulizer 200', which is intended to moved and adjusted relative to the endotracheal tube 340. Thus, the exhalation tube 130 and the sections 160, 170 that make it up should be constructed so that they can be extended or contracted along the same dimensional aspects as the inhalation tube 150 so that the Y-connector 340 is not strained in any direction but can maintain the position it had before manipulation of the lengths of the tube sections.

It will therefore be appreciated that the present invention provides a collapsible circuit for delivering medication to the patient through the ventilator system 100. It will further be appreciated that each of the extendable/contractable conduit sections is placed in its compact or retracted position when either the MDI 200 and/or the nebulizer 200' is not in use. It will also be appreciated that the exhalation tube 130 does not necessarily have to have an extendable/contractable structure to permit the length thereof to be varied. In this embodiment, the exhalation tube 130 can be a standard rigid tube or conduit.

Each of the extendable/contractable sections of the tubes 140, 150 of the present invention can include a lock mechanism or the like which permits the section of the tube that is extended or contracted to be locked in a specific position. For example, a clip type device can be used to lock the conduit section in place once the tube is at is desired length. To change the length of the tube, the clip is simply released and the tube is adjusted to a new length and then the clip can be relocked.

While the tubes 130, 150 are described above according to one embodiment as consisting of a bellows type wall structure, it will be understood that the tube can be formed of first and second parts that are slideable with respect to one another with one part being slidably inserted into the other part. By sliding one or both of the parts, the overall length of the tube can either be increased or decreased, thereby changing the location of the MDI 200 and/or nebulizer 200' relative to the endotracheal tube 340, as well as changing the holding chamber volume. It will further be appreciated that the first and second parts can also be fitted with a locking type mechanism so as to permit the position of the first part relative to the second part to be locked in place. For example, the first part can be at least partially received in the second part such that the first part at least partially surrounds the second part, with the first part having a number of axially aligned opening formed therein. Each opening corresponds to a different interior volume setting. The second part can include a biased projection that protrudes out from the exterior surface thereof and in one particular embodiment, the biased projection is a spring biased push button that can be depressed upon application of force and will return to its original biased position when the applied force is removed. When the second part is received in the first part, the biased projection is in a biased condition and is at least partially depressed and exerting a force against an inner surface of the first part until the projection comes into registration with one of the openings at which time, the biased nature of the projection causes the projection to fire into the opening, thereby locking the position of the first part relative to the second part. To freely adjust the interior volume of the holding chamber or any other section of either tube 130 or tube 150, the projection can simply be depressed until it clears the first part and then the second part can be moved relative to the first part in a direction toward the next desired opening at which time the projection is received in the opening, thereby locking the two parts in a different setting with a different interior volume.

As previously mentioned, each of the sections of the two tubes 130, 150 can be made of any number of different materials, including plastic, paper or even a metal so long as the interior volume thereof can be varied. According to one embodiment, the section of the tube 130, 150 can by cylindrical in shape with a series of ridges and recesses or valleys that alternate with one another so as to represent a bellows or accordion type structure. Alternatively, the tube section can be supported with a metal or plastic coil that includes multiple ring structures so as to support the material that defines the body of the tube section. The distances between any two adjacent ridges can be equal as in the case of a uniform structure or the distances can be different. In another embodiment, the tube section can be formed of a stiff corrugated plastic that preferably does not require any additional support to maintain the shape of the tube section.

Figure 4:
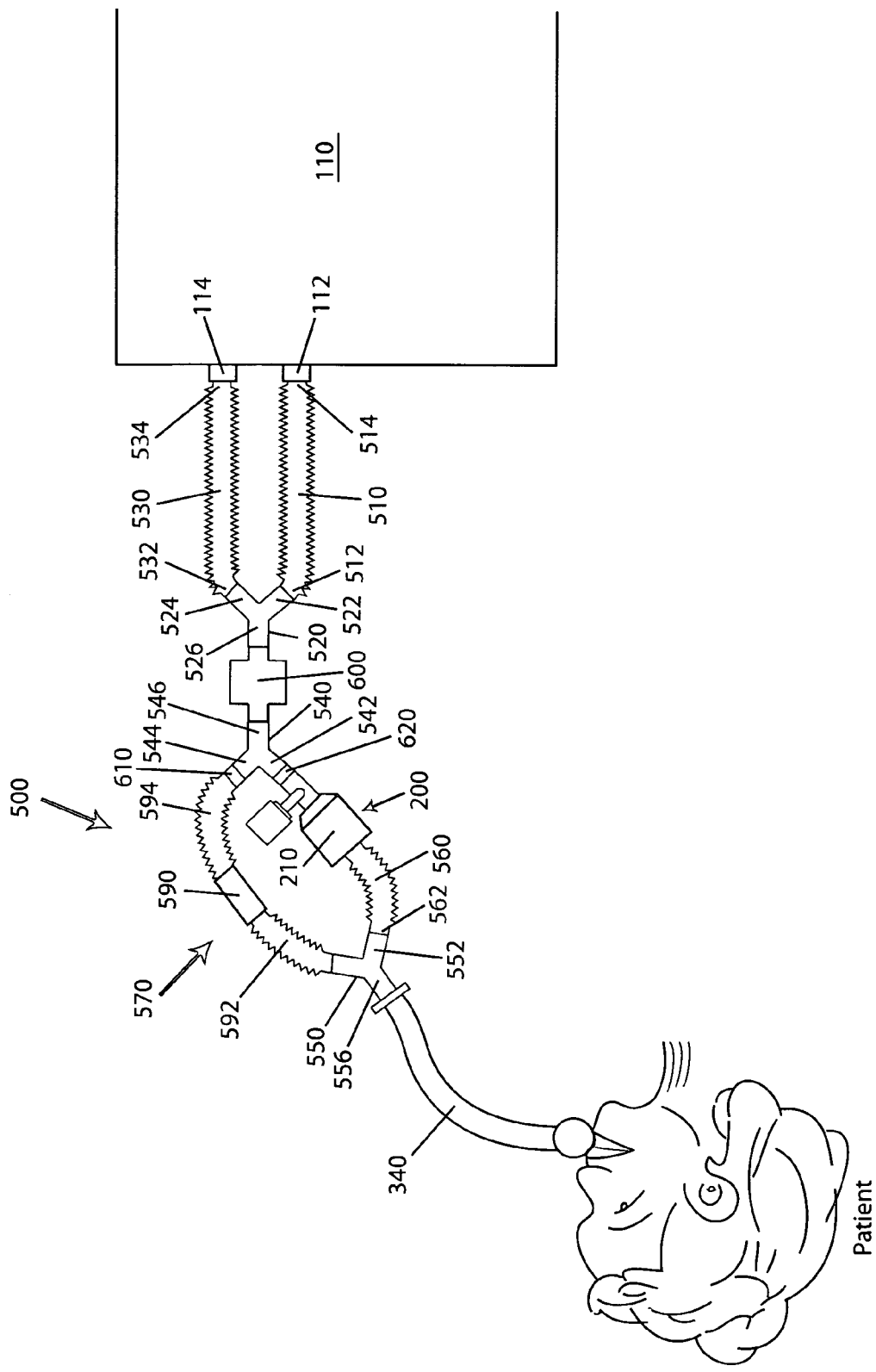
FIG. 4 is a cross-sectional side elevation view of a ventilator system according to a fourth embodiment.
Figure 5:
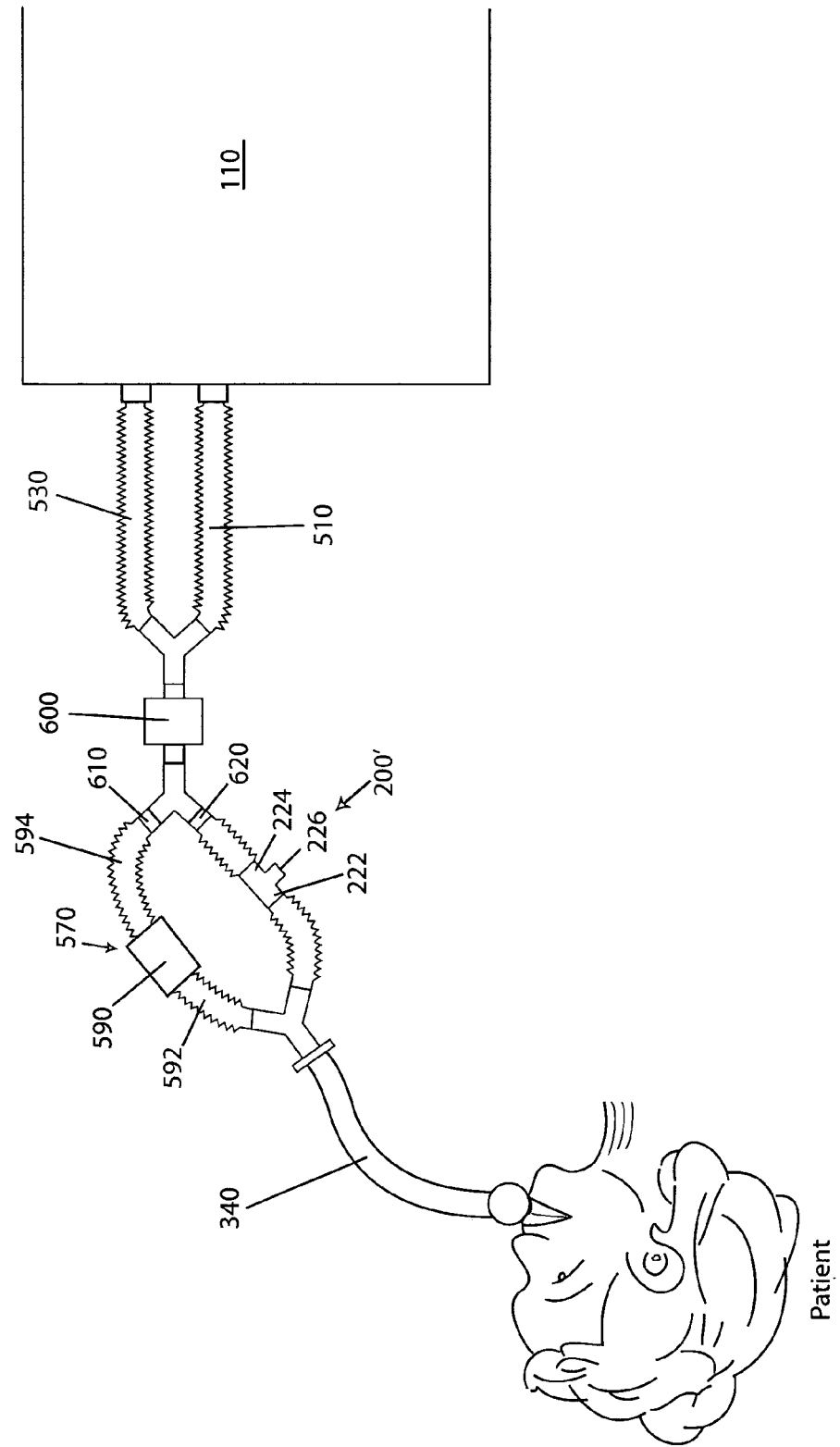
FIG. 5 is a cross-sectional side elevation view of a ventilator system according to a fifth embodiment.
Figure 6:
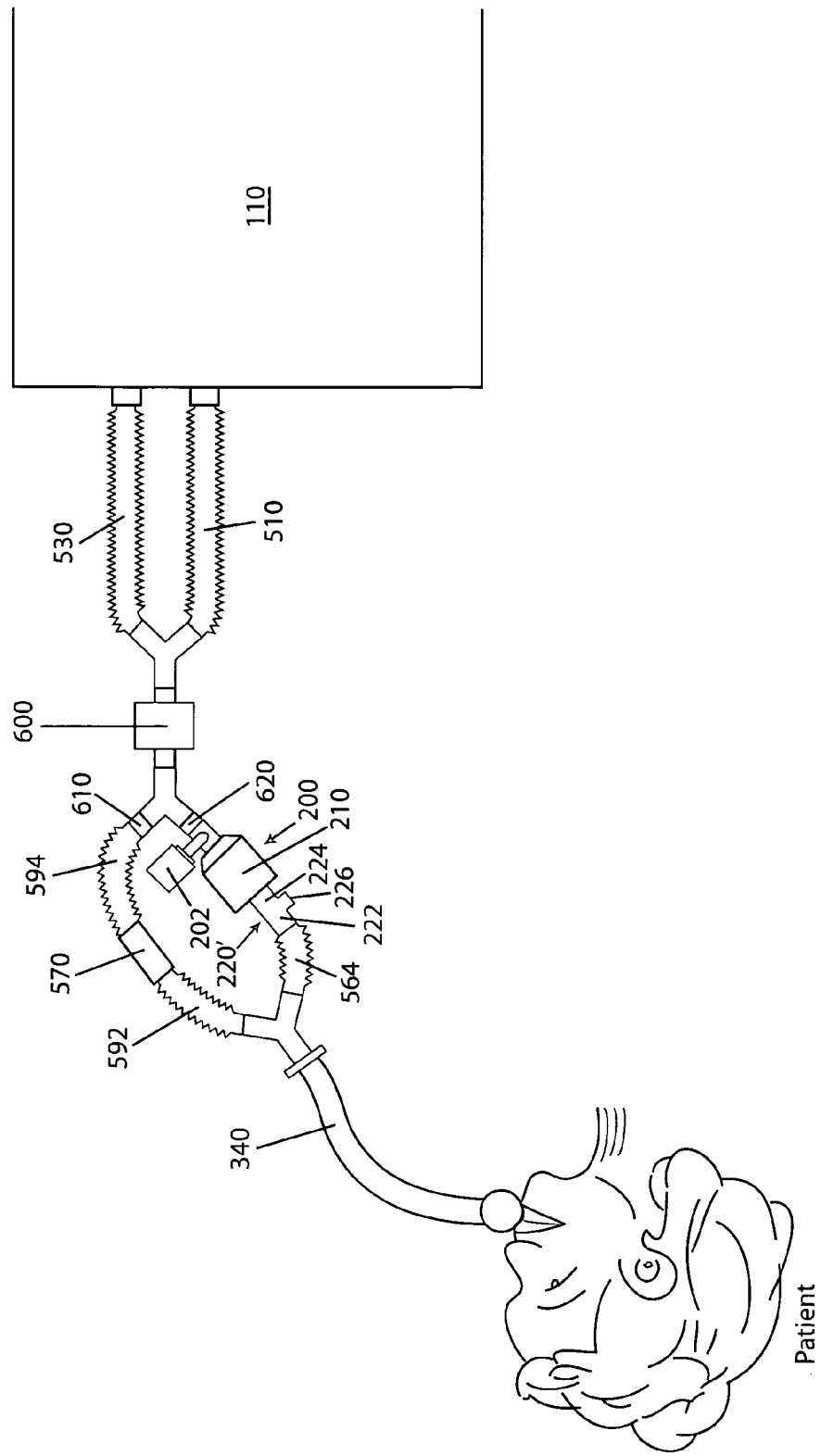
FIG. 6 is a cross-sectional side elevation view of a ventilator system according to a sixth embodiment.

Now referring to FIGS. 4-6 which illustrate yet another embodiment of the present invention and in particular, a ventilator system 500 is illustrated. The ventilator system 500 is similar to the system 100 with the exception that the system 500 does not include the humidifier unit 300. The components that are identical or substantially the same are numbered alike in both embodiments. The ventilator system 500 includes the ventilator device 110 with ports 112, 114. In this embodiment, a first inhalation conduit 510 is provided and includes a first end 512 that is attached to a first leg 522 of a first Y-connector 520 and a second end 514 that is attached to the inhalation port 112. A first exhalation conduit 530 is provided and includes a first end 532 that is attached to a second leg 524 of the first Y-connector 520 and a second end 534 that is attached to the exhalation port 114.

A third leg 526 of the Y-connector 520 is attached to one end of a heat moisture exchanger (HME) 600 that is used instead of a humidifier unit for heating and adding moisture to the compressed air. The HME 600 is available from any number of different commercial suppliers and consists of a unit that includes a heat and moisture exchanger filter for use with mechanical ventilators to provide heat and humidity while retaining bacterial/viral contaminants. Unlike the humidifier unit 200 that is placed only in the inhalation tube of the patient circuit in the first embodiment, the HME 600 is in fluid communication with both air that is inhaled by the patient as well as air that is exhaled by the patient.

The system 500 includes a second Y-connector 540 that includes first, second and third legs 542, 544, 546, respectively, with the third leg 546 being attached to the other end of the HME 600. A third Y-connector 550 is provided and includes first, second, and third legs 552, 554, 556, respectively, with the third leg 556 being connected to the endotracheal tube 340. Between the second and third Y-connectors 540, 550, the system 500 includes a second inhalation conduit 560 having a first end 562 that is attached to the first leg 552 of the third Y-connector 550 and a second end 564 opposite end 562. Also provided is a second exhalation conduit 570 having a first end that is attached to the second leg 554 of the third Y-connector 550 and a second end that is attached to the second leg 544 of the second Y-connector 540. In one embodiment, each of the first inhalation conduit 510 and the first exhalation conduit 530 has an extendable/contractable structure to permit the length thereof to be controllably varied as described in detail above with respect to the first embodiment. For example, the conduits 510, 530 can have a bellows type construction or the like.

Each of the second inhalation conduit 560 and the second exhalation conduit 570 is preferably formed so that they have an extendable/contractable structure, especially, the inhalation conduit 560. In the illustrated embodiment, the second exhalation conduit 570 has a rigid piece 590 that divides the conduit 570 into a first conduit section 592 and a second conduit section 594, each of which has an extendable/contractable wall structure. The rigid piece 590 provides a means for a user to easily grasp and alter the overall length of the second exhalation conduit 570. It will be appreciated that the rigid piece 590 can be eliminated and instead a single extendable/contractable structure can be provided.

In this embodiment, a first valve assembly 610 is provided within the second exhalation conduit 570. The first valve assembly 610 is preferably a one-way valve that serves to either permit or prevent the flow of exhaled gas to the HME 600. The first valve assembly 610 can be disposed at the interface between the second conduit section 594 and the second leg 544 of the second Y-connector 540. As the patient exhales, the first valve assembly 610 opens to permit the exhaled to flow into the HME 600 and conversely, when the patient inhales, the first valve assembly 610 closes to close off the second exhalation conduit 570 from the HME 600.

Within the second inhalation conduit 560, one or more devices or means for delivering aerosolized medication to the conduit 560 is provided similar to the first system 100. More specifically, the device can be the MDI 200 or the nebulizer 200' or a combination of both in series with respect to one another. For purpose of illustration only, FIG. 6 shows the system 500 as including both the MDI 200 and the nebulizer 200'; however, it will be understood that the system 500 can include only one of the devices 200, 200' as shown in FIGS. 4 and 5.

In the embodiment of FIG. 6, the MDI 200 includes the spacer 210 and is arranged such that the nozzle portion 202 thereof is fluidly attached to the first leg 542 of the second Y-connector 540 and the spacer 210 is attached to one leg 224 of the T connector 220, while the other leg 222 of the T connector 220 is attached to the second end 564 of the second inhalation conduit 560. The third leg 226 of the T connector 220 is the one that is connected to a continuous source of gas that is used to aerosolize the medication. Once again, the source of gas is preferably an outside, external source of gas that is not associated with the ventilator device 110 itself; however, as previously mentioned, the ventilator device 110 can be modified to have a port that continuously supplies gas both during inhalation and exhalation. When the nebulizer 200' is not in use, the third leg 226 is simply capped.

In this embodiment, a second valve assembly 620 is provided in fluid communication with the inhalation flow path. The second valve assembly 620 is preferably a one-way valve that serves to either permit or prevent the flow of inhaled gas from the HME 600 to the endotracheal tube 340. The second valve assembly 620 can be disposed at the interface between the nozzle 202 of the MDI 200 and the first leg 542 of the second Y-connector 540. As the patient inhales, the second valve assembly 620 opens to permit the gas to flow from the HME 600 and into the device that contains the means for aerosolizing the medication and then ultimately into the endotracheal tube 340 and conversely, when the patient exhales, the second valve assembly 620 closes to close off the second inhalation conduit 560 from the HME 600.

In conventional ventilator systems that include an HME, the HME unit directly connects to the endotracheal tube 340 and the MDI or nebulizer, when used, is inserted between the endotracheal tube 340 and the HME unit. One important consideration is that waste gases, such as $CO_2$, must be removed from the ventilator system 500 as the patient breathes. In the present system 500, this is accomplished by incorporating the two one way valves 610, 620 within the system. The two one way valves 610, 620 serve to limit and selectively route either the exhaled gas or the inhaled gas to the HME 600 depending upon the breathing action of the patient.

As with the first embodiment, the system 500 according to the present invention permits the distance from the endotracheal tube 340 to the MDI 200 and/or the nebulizer 200' to be altered by simply either extending or contracting the second inhalation conduit 560 depending upon whether it is desired to locate the MDI 200 and/or the nebulizer 200' either further away from the patient, as is the case when the patient is a larger adult, or closer to the patient, as is the case when the patient is a small child. In order to accommodate the change in the length of the second inhalation conduit 560, the length of the exhalation conduit 570 is most likely also changed in the same manner. Thus, if the inhalation conduit 560 is expanded, then the exhalation conduit 570, will similarly be expanded, either by expanding the first conduit section 592 and/or the second conduit section 594.

Figure 7:
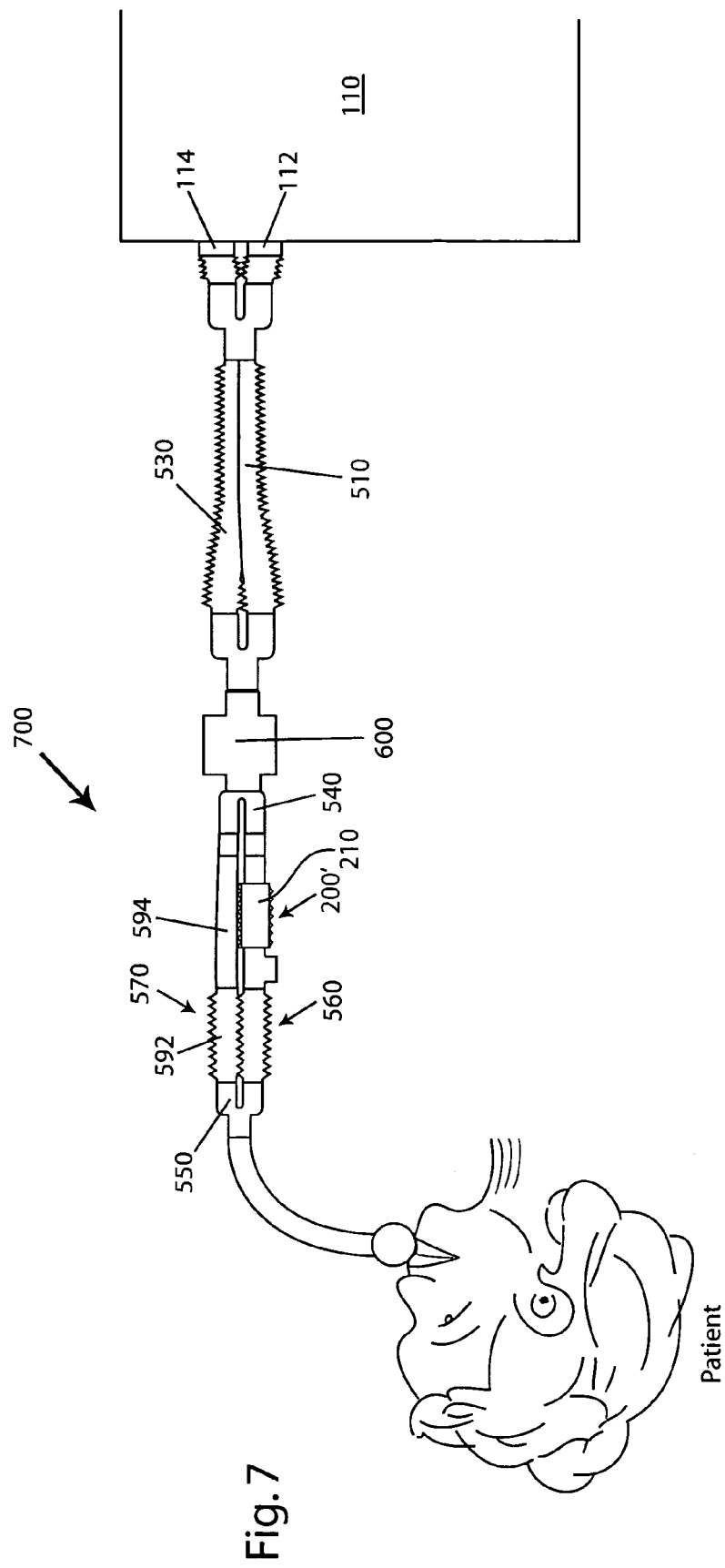
FIG. 7 is a cross-sectional side elevation view of a ventilator system according to a seventh embodiment.

Now referring to FIG. 7, a ventilator system 700 according to a third embodiment is illustrated. The system 700 is very similar to the system 500; however, some of the conduits have been integrated with one another so as to share a common wall. In order, some of the conduits have been merged from a pair of conduit structures into a single conduit structure. For example, the first inhalation tube 510 and the first exhalation tube 530 can be merged together and share a common wall. Thus, when it is desired to change the distance from the HME 600 to the ventilator device 110, only a single action due to the combined nature of the two conduits 510, 530. In the previous embodiment, each of the conduits 510, 530 required its own adjustment and manipulation in order to change the length thereof.

In addition, a portion of the second inhalation conduit 560 and the second exhalation conduit 570 is likewise combined into a single integrated conduit structure. For example and as shown, the second inhalation conduit 560 shares a common wall with the first conduit section 592 of the second exhalation conduit 570. However, the second conduit section 594 is separate and spaced from and free to move relative to the MDI 200 and/or nebulizer 200' which is connected between the inhalation conduit 560 and the second Y-connector 540. This arrangement permits the spacer 210 to be able to freely extend and contract without any interference from the second conduit section 594. While the inhalation conduit 560 and the first conduit section 592 can each extend up to a number of feet, e.g., 5 feet, the spacer 210 only extends a fraction thereof. For example, the spacer 210 can be constructed so that when it fully extends, the spacer 210 has a length of about 6 inches or so.

Once again, since the inhalation conduit 560 and the first conduit section 592 share a common wall and are in effect, a single conduit structure, one a single step is needed to either extend or contract both conduits 560, 592 since they are integrated with one another. This reduces the number of steps and the time needed to properly position the MDI 200 and/or the nebulizer 200' in the desired location.

It will be understood that all of the conduits (exhalation and inhalation) in each of the described embodiments are elongated hollow structures that can have any number of different cross-sectional shapes. For example, the conduit can have a circular cross-section; a rectangular cross-section, a square cross-section, an oval cross-section, etc.

Moreover, it will be understood that for each of the above described embodiments, the ventilator system includes one or more means for delivering medication into the inhalation conduit of the patient circuit. For example, an MDI can be incorporated into the inhalation conduit for delivering a metered dose of medication or in another embodiment, the inhalation conduit can include a nebulizer T connector for attachment to an external source of gas for generating the aerosolized particles of medication. In yet another embodiment, both the MDI and nebulizer are incorporated into the inhalation conduit and are positioned side-by-side to permit the physician to use either of these devices to deliver the medication. When the devices are not in use, each device can be capped. This arrangement is convenient to the physician since the MDI and the nebulizer already form a part of the inhalation circuit and thus, the physician does not have to take a part the ventilator system to incorporate and add one or more of these devices for delivering the medication. Not only is time saved by eliminating this step but also the risk of infection and contamination is eliminated.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A ventilator system comprising:
    a ventilator device having an inhalation port and exhalation port;
    a patient conduit for delivering to and removing gas from the patient;
    an exhalation conduit fluidly connected to the exhalation port and the patient conduit;
    an inhalation conduit fluidly connected to the inhalation port and the patient conduit, the inhalation conduit at least in part defining a holding chamber; and a device for generating aerosolized medication, the device being fluidly connected to the inhalation conduit so that the aerosolized medication is delivered to the patient as the patient inhales;

wherein at least a first inhalation conduit section of the inhalation conduit that is located between the device and the patient conduit has a variable length to position the device for generating aerosolized medication a predetermined distance from the patient conduit, the first inhalation section being defined by a body that is both extendable and contractable along a length of the body to permit a volume of the holding chamber to be varied and thereby provides a means for adjusting the strength of the dose of medication, wherein the first inhalation conduit section includes a plurality of markings each corresponding to a volume of the holding chamber based on the length of the first inhalation conduit section, the markings thus providing settings to assist in adjusting the strength of the medication that is generated and delivered to the patient from the device.

2. The ventilator system of claim 1, further comprising a humidifier unit in fluid communication with the inhalation conduit and the inhalation port for receiving compressed air from the ventilator device and then heating and adding moisture to the compressed air.

3. The ventilator system of claim 1, wherein the inhalation conduit further includes a second inhalation conduit section, with the device being fluidly attached to the two conduits sections such that the first inhalation conduit section extends from the patient conduit to the device and the second inhalation conduit section extends from the device to the ventilator device.

4. The ventilator system of claim 3, wherein at least the first inhalation conduit section has a length that can be varied due to a wall structure that is both extendable and contractable along a length thereof.

5. The ventilator system of claim 3, wherein each of the first and second inhalation conduit sections has a length that can be varied due to an extendable and contractable wall structure of each conduit.

6. The ventilator system of claim 5, wherein the wall structure of each conduit comprises a bellows type wall structure that expands from between 1 inch to about 6 feet.

7. The ventilator system of claim 1, wherein the device comprises at least one of a metered dose inhaler (MDI) and a nebulizer.

8. The ventilator system of claim 1, wherein the device comprises a metered dose inhaler (MDI) that has a spacer in fluid communication with the inhalation conduit, the spacer having a variable volume.

9. The ventilator system of claim 8, wherein the spacer has a length that can be varied due to a wall structure that is both extendable and contractable along a length thereof.

10. The ventilator system of claim 1, wherein the exhalation conduit includes two sections that each has a variable length with a rigid fixed length connector being disposed therebetween and fluidly connecting the two sections.

11. A ventilator system comprising:

a ventilator device having an inhalation port and exhalation port;

a patient conduit for delivering to and removing gas from the patient;

a heat moisture exchanger in fluid communication with the ventilator device;

a first exhalation conduit fluidly connected to the exhalation port and the heat moisture exchanger;

a first inhalation conduit fluidly connected to the inhalation port and the heat moisture exchanger;

a second exhalation conduit fluidly connected to the patient conduit and the heat moisture exchanger;

a second inhalation conduit fluidly connected to the patient conduit and the heat moisture exchanger; and a device for generating aerosolized medication, the device being fluidly connected between the second inhalation conduit and the heat moisture exchanger so that the aerosolized medication is delivered to the patient as the patient inhales;

wherein at least the second inhalation conduit has a variable length due to the second inhalation conduit being having a body that is both extendable and contractable along the length thereof to permit positioning of the device for generating aerosolized medication a predetermined distance from the patient conduit and thereby permits a volume of the holding chamber to be varied and thereby provides a means for adjusting the strength of the dose of medication, wherein the second inhalation conduit section includes a plurality of markings each corresponding to a volume of the holding chamber based on the length of the second inhalation conduit section, the markings thus providing settings to assist in adjusting the strength of the medication that is generated and delivered to the patient from the device.

12. The ventilator system of claim 11, wherein the heat moisture exchanger is attached to first and second Y-connectors, the first Y-connector being fluidly attached to the first inhalation and exhalation conduits, the second Y-connector being fluidly attached to the second exhalation conduit and the device for generating aerosolized medication.

13. The ventilator system of claim 12, further including a third Y-connector fluidly attached to the second exhalation conduit, the second inhalation conduit and the patient conduit.

14. The ventilator system of claim 11, further including: a first valve assembly in fluid communication with the second exhalation conduit and the heat moisture exchanger and moveable between an open position when the patient exhales and a closed position when the patient inhales; and a second valve assembly in fluid communication with the second inhalation conduit and the heat moisture exchanger and moveable between an open position when the patient inhales and a closed position when the patient exhales.

15. The ventilator system of claim 14, wherein each of the first and second valves comprises a one-way valve.

16. The ventilator system of claim 11, wherein the second inhalation conduit section has a length that can be varied due to a wall structure that is both extendable and contractable along a length thereof.

17. The ventilator system of claim 11, wherein each of the first and second inhalation conduits and the first and second exhalation conduits has a length that can be varied due to an extendable and contractable wall structure of each conduit.

18. The ventilator system of claim 17, wherein the wall structure of each conduit comprises a bellows type wall structure that expands from between 1 inch to about 6 feet.

19. The ventilator system of claim 11, wherein the device for generating aerosolized medication comprises at least one of a metered dose inhaler (MDI) and a nebulizer.

20. The ventilator system of claim 11, wherein the device for generating aerosolized medication comprises a metered dose inhaler (MDI) that has a spacer in fluid communication with the inhalation conduit, the spacer having a variable volume.

21. The ventilator system of claim 19, wherein the nebulizer includes a nebulizer connector that is connected to an outside source of gas so that gas continuously flows into the nebulizer to form the aerosolized medication that continuously flows into the inhalation conduit.

22. The ventilator system of claim 21, wherein the connector comprises a T-connector with a first leg of the T-connector being connected to the second inhalation conduit; a second leg being attached to one of another section of the second inhalation conduit and the MDI; and a third leg being attached to the outside source of gas.

23. The ventilator system of claim 22, wherein both the MDI and the nebulizer are provided within the inhalation conduit, the MDI being fluidly attached to the nebulizer.

24. The ventilator system of claim 11, wherein the second exhalation conduit includes two sections that each has a variable length with a rigid fixed length connector being disposed therebetween and fluidly connecting the two sections.

25. The ventilator system of claim 11, wherein the first exhalation conduit and the first inhalation conduit share a common wall so as to form a single conduit structure.

26. The ventilator system of claim 11, wherein a portion of the second exhalation conduit and the second inhalation conduit share a common wall so as to form a single conduit structure.

27. A ventilator system comprising:
   a ventilator device having an inhalation port and exhalation port;
   a patient conduit for delivering to and removing gas from the patient;
   an exhalation conduit fluidly connected to the exhalation port and the patient conduit;
   an inhalation conduit fluidly connected to the inhalation port and the patient conduit;
   a device for generating aerosolized medication, the device being fluidly connected to the inhalation conduit so that the aerosolized medication is delivered to the patient as the patient inhales; wherein at least a first inhalation conduit section of the inhalation conduit that is located between the device and the patient conduit has a variable length due to the first inhalation conduit section being formed of a body that is both extendable and contractable along the length thereof to position the device for generating aerosolized medication a predetermined distance from the patient conduit, the variable length of the first inhalation conduit section permitting a volume of the holding chamber to be varied and thereby provides a means for adjusting the strength of the dose of medication, the inhalation conduit including a second inhalation conduit section located between the device and the ventilator device, wherein at least a first section of the exhalation conduit has a variable length;
   a humidifier unit in fluid communication with the inhalation conduit and the inhalation port for receiving compressed air from the ventilator device and then heating and adding moisture to the compressed air;
   a first heating wire that is incorporated into an inner wall of the second inhalation conduit section in a coiled manner such that a length of the second inhalation conduit section can be varied; and
   a second heating wire that is incorporated into an inner wall of the first section of the exhalation conduit in a coiled manner such that a length of the first section of the exhalation conduit can be varied.

* * * * *